US00PP15661P2

(12) United States Plant Patent
Friday

(10) Patent No.: US PP15,661 P2
(45) Date of Patent: Mar. 15, 2005

(54) NECTARINE TREE NAMED 'P.F. 11 NECTARINE'

(50) Latin Name: *Prunus persica*
Varietal Denomination: P.F. 11 Nectarine

(76) Inventor: Paul Jan Friday, P.O. Box 850, Coloma, MI (US) 49038

( * ) Notice: Subject to any disclaimer, the term of this patent is extended or adjusted under 35 U.S.C. 154(b) by 11 days.

(21) Appl. No.: 10/712,139

(22) Filed: Nov. 14, 2003

(51) Int. Cl.[7] ..... A01H 5/00
(52) U.S. Cl. ..... Plt./192
(58) Field of Search ..... Plt./192

*Primary Examiner*—Kent Bell
*Assistant Examiner*—W C Haas

(57) ABSTRACT

A new and distinct variety of nectarine, *Prunus persica,* tree having the following unique combination of desirable features:

1. Producing a very firm fruit having a resilient flesh texture.
2. Blossoms are non-showy when in full bloom.
3. A substantially spherical fruit with yellow flesh having red mottling.
4. A mid-season nectarine variety that matures after 'Redhaven' (unpatented) and which has good storage and shelf life.

1 Drawing Sheet

Botanical classification: *Prunus persica.*
Variety denomination: 'P.F. 11 Nectarine'.

ORIGIN OF VARIETY

The new nectarine tree {hereinafter referred to as the P.F. 11 Nectarine tree} was originated by Paul Friday in an experimental orchard, which is maintained for the purposes of breeding peach trees, located in Coloma, Mich., USDA Zone 6a. Coloma is located in the southwest section of Michigan.

In an ongoing mass selection breeding program, superior seedlings of unrecorded parentage are maintained as seed sources for the production of seeds which are collected and planted in mass. The seeds producing parent trees are maintained solely as proprietary trees for breeding purposes and have not been released from the experimental orchard, where such trees can be evaluated for their adaptability to local and regional growing conditions. Seeds resulting from open pollination of the trees in the experimental orchard are regularly planted in mass to produce new populations of seedlings which are cultured and monitored to maturity. Trees with superior attributes are retained for further observation and testing, and contribute seeds to advancing generations of new populations of seedlings.

The tree of this application, 'P.F. 11 Nectarine', was a single plant from one such a seedling population, and was based on the numerous superior genetic attributes of this tree which are described in the botanical description to follow. While not comprehensive, the details of the botanical description to follow are believed to be a reasonably complete botanical description of the tree of this disclosure.

ASEXUAL REPRODUCTION OF THE VARIETY

The new and distinct variety of nectarine tree was asexually propagated by budding as performed in an experimental orchard, located in Coloma, Mich. The asexual propagation demonstrates that such reproduction of the characteristics of the tree are consistent and are established and transmitted through succeeding propagation.

SUMMARY OF THE VARIETY

The new and distinct variety of nectarine tree is of moderate upright growth and a regular and productive bearer of nectarines. The blossoms are characterized by being contracted or partially spread when in full bloom.

The blossoms of the present nectarine tree at full bloom may be characterized as being showy. More specifically, the blossoms of the present nectarine tree have angularly spaced five-blossom petals projecting upwardly at an inclined angle so as to form a blossom having a diameter of about 1½" measured across the blossoms. The typical showy blossom as exemplified for example by the "Loring" (non-patented) peach has five (5) radically extending and angularity spaced petals projecting upwardly at a relatively steep inclined angle so that the diametrical measurement across the outer edges of the petals is also about 1½".

The flesh of the fruit of the present nectarine tree is firm and is yellow with a minimum of red around the pit.

The skin is smooth and is of dark red color over almost 100 percent (100%) of its surface at full maturity. The fruit is large with an average diameter of 2½".

It is noteworthy that the fruit of this tree is further characterized as having smooth, gently rounded cheeks at the blossom end of the fruit. These protrude to form fruit surfaces higher than the blossom point. This characteristic reduces fruit damage in harvest, shipping and storage, by reducing the exposure of and damage to the apical blossom protrusion in handling. Thus breaching of the skin and formation of an entry point for microorganisms which cause rot in many other commercially important nectarines varieties harvested in the same production period is avoided in this fruit.

The fruit has a firm flesh and may be described as resilient to the extent that the flesh is yieldable and restorable to its original state when subjected to impact forces, which may cause permanent deformities in nectarines of the commercial varieties. The firmness of the fruit facilitates handling and packaging of the nectarines without damaging the same for shipment. This results in less spoilage and also increases the shelf life.

BRIEF DESCRIPTION OF THE PHOTOGRAPHS

The accompanying photographic illustrations of the new variety show the following:

The top photograph depicts well-rounded fruit showing an unpronounced suture And a well-rounded blossom end. One specimen of the fruit is bisected at a ninety-degree Angle to the plane of the suture with the stone retained in half showing its freestone characteristic and clear yellow flesh and a minimum of red around the pit. A tape measure is present indicating the large size of the fruit.

The bottom photograph depicts leaves of medium length, and width, having notably very fine serrated margins. A tape measure is present, demonstrating the medium size of the leaves.

DESCRIPTION OF VARIETY

The detailed botanical description of the foliage and fruit of the new variety of nectarine tree as grown on its own roots is based upon observations of the specimens grown at Coloma, Mich. with the color terminology, other than the terminology expressed in common terms, in accordance with the Pantone Matching System (PMS) as used internationally to identify printed colors.

Botanical classification: *Prunus persica* cultivar 'P.F. 11 Nectarine'.

Tree:
- *Age.*—Twelve (12) years.
- *Height.*—Unpruned 11'.
- *Width.*—Unpruned 11'.
- *Size.*—Medium.
- *Vigor.*—Medium.
- *Density.*—Medium.
- *Form.*—Spreading to upright.
- *Production.*—Good, requires heavy thinning then produces about 1½ bushels per tree per year.
- *Bearer.*—Excellent.
- *Disease resistance to bacterial leaf and fruit spot.*—Particularly resistant.

Trunk:
- *Bark.*—Gray (405).
- *Size.*—Medium.
- *Diameter.*—5¼" diameter at 20" above the ground at 12 years of age.
- *Surface.*—Semi-rough.
- *Lenticels.*—Pronounced.
- *Lenticels color.*—471.
- *Lenticels size.*—¼"–⅜".

Branches:
- *Size.*—Medium — 2¼" diameter at 4" from trunk union.
- *Surface.*—Semi-rough.
- *Lenticels per square inch on branch.*—Usually six (6).
- *Lenticels color.*—473.
- *Lenticels size.*—⅛"–¼".
- *Crotch angles.*—85 degree angles.
- *Branch color.*—Gray (423).
- *Internode length.*—¾".

Leaves:
- *Size.*—5½" long — 1½" wide.
- *Color.*—Top of leaf 575, bottom of leaf 385.
- *Form.*—Lanceolate.
- *Thickness.*—Medium.
- *Texture.*—Glabrous.
- *Margin.*—Finely Serrate.
- *Petiole length.*—7/16".
- *Gland.*—Approximately 2 on either side of the petiole and at basal part of the leaf.
- *Gland color.*—Dark red.
- *Gland shape.*—Cupped.

Flower buds:
- *Size.*—½" long — ¼" wide.
- *Shape.*—Ovoid.
- *Color.*—217.

Flowers:
- *Blooming period.*—Apr. 23, 2003 to Apr. 27, 2003.
- *Bloom size.*—1½" diameter.
- *Size of petals.*—¾" long — ½" wide.
- *Shape of petals.*—Slightly cupped.
- *Petal color.*—250.
- *Number of petals per flower.*—Five (5).
- *Sepal size.*—¼" long — 3/16" wide.
- *Sepal shape.*—Very slightly cupped.
- *Sepal color.*—384.
- *Number of anthers.*—28.
- *Anther color.*—131.
- *Number of stamens.*—28.
- *Stamen length.*—7/16".
- *Stamen color.*—217.
- *Pistil length.*—½".
- *Pistil color.*—102.
- *Pollen.*—Present, self fertilizing.
- *Flower color.*—250.
- *Flowers per cluster.*—2–3.
- *Fragrance.*—Very slight.

Fruit:
- *Maturity when described.*—Full mature.
- *Date of first picking.*—Aug. 5, 2003.
- *Date of last picking.*—Aug. 10, 2003.
- *Size.*—Average 2½" diameter.
- *Form.*—Oblate Sphere.
- *Suture.*—Not pronounced.
- *Weight.*—Average 6.9 oz.

Skin:
- *Thickness.*—Medium.
- *Texture.*—Tough, tenacious to skin.
- *Tendency to crack.*—None.
- *Down.*—None.
- *Color.*—All red (187).

Flesh:
- *Texture.*—Firm.
- *Ripens.*—Uniform.
- *Aroma.*—Good.
- *Eating quality.*—Excellent.
- *Color.*—Yellow (131).
- *Pit cavity color.*—Yellow (136).

Stone:
- *Type.*—Freestone.
- *Size.*—1 5/16" long, 1 1/16" wide, ¾" thick.
- *Form.*—Ovoid.
- *Base.*—Straight.
- *Apex.*—Rounded but with a very sharp point.
- *Sides.*—Uneven.
- *Surface.*—Furrowed.
- *Color.*—Unusually light colored (155).
- *Tendency to crack.*—About 5%.
- *Kernel.*—⅝" long, 7/16" wide, ⅛" thick.

Use: Dessert.
Shipping quality: Very Good.
Keeping quality: Good.

The tree and its fruit herein described may vary in slight detail as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of nectarine tree as herein illustrated and described.

* * * * *

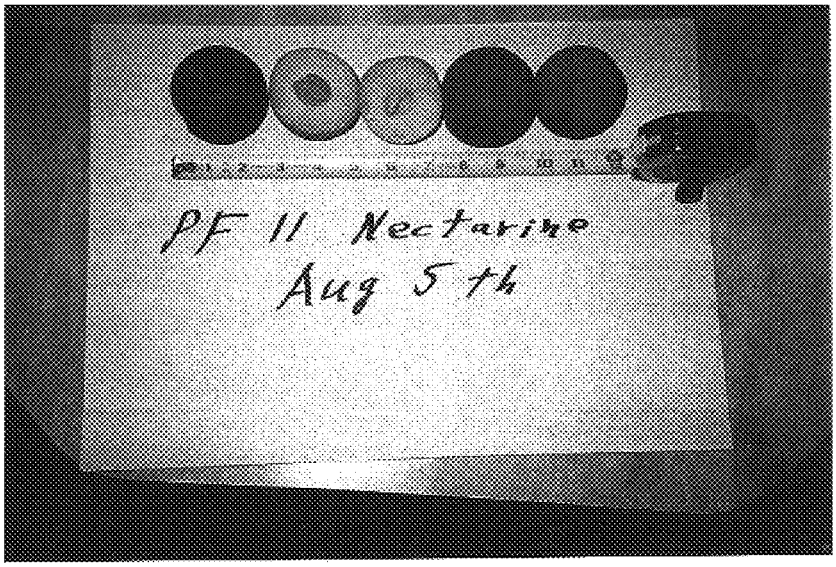
PF 11 Nectarine
Aug 5th
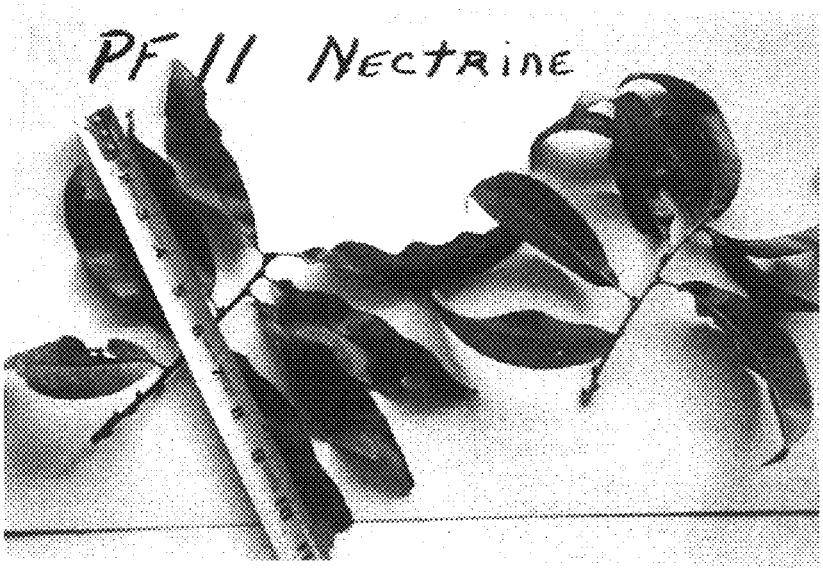
PF 11 NECTRINE